(12) United States Patent
Cromwell et al.

(10) Patent No.: US 7,643,146 B2
(45) Date of Patent: Jan. 5, 2010

(54) METHODS AND APPARATUS FOR REDUCING NOISE IN SCATTEROMETRY MEASUREMENTS

(75) Inventors: Evan F. Cromwell, Redwood City, CA (US); Steven C. Miller, Union City, CA (US); Robert T. Trujillo, Saratoga, CA (US); Paul B. Comita, Menlo Park, CA (US)

(73) Assignee: Blueshift Biotechnologies, Inc., Sunnyvale, CA (US)

( * ) Notice: Subject to any disclaimer, the term of this patent is extended or adjusted under 35 U.S.C. 154(b) by 76 days.

(21) Appl. No.: 11/336,388

(22) Filed: Jan. 20, 2006

(65) Prior Publication Data

US 2007/0171417 A1 Jul. 26, 2007

(51) Int. Cl.
*G01N 21/47* (2006.01)
(52) U.S. Cl. .................................. 356/446; 356/445
(58) Field of Classification Search ............ 356/73, 356/244–246, 445–446, 432–442; 422/99, 422/102, 104; 435/288.2–288.4
See application file for complete search history.

(56) References Cited

U.S. PATENT DOCUMENTS

| | | | |
|---|---|---|---|
| 4,599,315 A | 7/1986 | Terasaki et al. | |
| 4,657,867 A | 4/1987 | Guhl et al. | |
| 5,082,628 A * | 1/1992 | Andreotti et al. | 422/82.08 |
| 6,063,338 A | 5/2000 | Pham et al. | |
| 6,074,614 A | 6/2000 | Hafeman et al. | |
| 6,730,520 B2 | 5/2004 | Coassin et al. | |
| 6,861,035 B2 | 3/2005 | Pham et al. | |
| 2001/0007496 A1 | 7/2001 | Modlin et al. | |
| 2003/0128371 A1 | 7/2003 | Vaux et al. | |

(Continued)

FOREIGN PATENT DOCUMENTS

DE 4405375 A1 8/1995

(Continued)

OTHER PUBLICATIONS

International Search Report dated Jun. 18, 2007 from corresponding International Application No. PCT/US2007/001512.

(Continued)

*Primary Examiner*—Gregory J Toatley, Jr.
*Assistant Examiner*—Tri T Ton
(74) *Attorney, Agent, or Firm*—Weaver Austin Villeneuve & Sampson LLP

(57) ABSTRACT

Methods and apparatus for performing scatterometry measurements of biological samples as described herein. A substrate having formed therein one or more sample wells is provided. Each sample well is configured to hold a sample solution containing objects that are to be characterized based on their light scattering properties. One or more sample solutions are dispensed into the sample wells. A specular reflection reducing element is applied to at least some of the sample solutions in the sample wells to decrease reflections of light into one or more detectors. A light beam is directed from a light source onto the objects in the sample wells. Light scattered by the objects in the sample wells is collected and transmitted to one or more detectors. The signal from the detectors is analyzed to detect the one or more characteristics of the one or more samples.

16 Claims, 8 Drawing Sheets

U.S. PATENT DOCUMENTS

| | | |
|---|---|---|
| 2005/0019221 A1 | 1/2005 | Shumate et al. |
| 2005/0046847 A1 | 3/2005 | Cromwell et al. |
| 2005/0112773 A1 | 5/2005 | Vuong |
| 2005/0136528 A1 | 6/2005 | Bahnson et al. |
| 2005/0214174 A1 | 9/2005 | Pham et al. |
| 2005/0287040 A1* | 12/2005 | Giebeler et al. .......... 422/82.08 |

FOREIGN PATENT DOCUMENTS

| | | |
|---|---|---|
| JP | 05181068 | 7/1993 |
| WO | WO 02/087763 A1 | 11/2002 |

OTHER PUBLICATIONS

Written Opinion dated Jun. 18, 2007 from corresponding International Application No. PCT/US2007/001512.

Buhn J B et al., "A Molecular Dynamics Study of a Liquid-Liquid Interface: Structure and Dynamics", found in Fluid Phase Equilibria, Elsecier, vol. 224, No. 2, on Oct. 1, 2004, pp. 221-230.

* cited by examiner

Add Black Coverslip to Image

Overfill with Suitable Solution

Colonies Grown in Media

US 7,643,146 B2

METHODS AND APPARATUS FOR REDUCING NOISE IN SCATTEROMETRY MEASUREMENTS

BACKGROUND

This invention relates to measuring properties of biological samples using scatterometry techniques.

Cytometry refers to the measurement of cells. These measurements can refer to a cell's physical properties (shape, volume, and so on) or of the cell's biochemical properties (protein content, lipid content, and so on). One common class of cytometry measurements is light scattering measurements, which are also referred to as scatterometry metrology. Scatterometry techniques can be used in a range of biological applications, ranging from the assessment of bacterial concentration in a suspension to the resolution of the fine structure of single cells. Scatterometry is often a preferred method for making measurements on single cells in situations where fluorometry (i.e., staining the cells with fluorophores, exciting them, and studying the scattered light) is not feasible, for example, when a population of live cells is studied and the fluorophore is toxic to the cells. Scatterometry also allows measurements to be made on any type of cells or particles, not only on cells that express a fluorescent protein, as is the case with fluorescent measurements.

When a single cell intersects a light beam, typically a laser beam, some of the light is scattered out of the beam. The amount of light that is scattered by a cell is a complex function of the cell's size, shape and refractive index. The sensitivity of a measurement to each of these factors is dependent upon the range of angles over which the scattered light is collected. For example, light scattered at small angles (i.e. forward light scatter) is most dependent upon the size of the scattering particle.

A common problem in scatterometry measurements is the existence of unwanted reflections, scatter and artifacts in the signal that is received by the detector. One such problem is illustrated in FIG. 1, which shows how light is reflected from the meniscus of a solution in a sample well and is received by the detector. FIGS. 2 and 3 show the manifestation of these meniscus reflections when the sample is imaged. The meniscus reflections can be seen as various types of large "half-moon" shaped features in the left hand side of FIGS. 2 and 3. These reflections are due to the difference in refractive index between the sample liquid and air at the meniscus interface and the shape results from the angle of the meniscus where the incoming laser light hits the meniscus, as well as the well's wall shape. Certain types of wells have reflections from the walls themselves too.

As the skilled reader realizes, these reflections are highly undesirable as they may obscure valuable scattering data originating from the sample. There is therefore a need for an improved method and apparatus for reducing specular reflections, for example, from the meniscus and improving the abilities to view the cells in the sample solution using laser scatterometry techniques.

SUMMARY

Various aspects of the invention meet some or all of the challenges set forth above. In general, in one aspect, the invention provides methods and apparatus, including computer program products, implementing and using techniques for performing scatterometry measurements pertaining to one or more characteristics of one or more biological samples. The apparatus has a light source, a flat substrate, one or more illumination optical elements and one or more collection optical elements. The substrate has one or more sample wells, each of which is configured to hold a sample. Each of the sample wells is covered with a specular reflection reducing element. The illumination optical elements direct a light beam from the light source onto the sample wells. The collection optical elements collect light originating from within the sample wells and transmit the collected light to one or more detectors.

Advantageous implementations can include one or more of the following features. The specular reflection reducing element can be a gel, an oil, a solid, a plastic, a glass, a flexible solid, a hard solid, or a waxy-like material. The specular reflection reducing element can be configured to reduce a curvature of a meniscus of the sample solution. The specular reflection reducing element can be configured to absorb light in a wavelength region corresponding to the wavelength region of the light source in order to further reduce reflections. The specular reflection reducing element can have an index of refraction close to or equal to the index of refraction of the sample solution. The specular reflection reducing element can be sterilized prior to applying the specular reflection reducing elements to the at least some sample solutions. Applying the specular reflection reducing element can include applying the specular reflection reducing element at an angle with respect to the sample solution's surface so as to avoid trapping of air bubbles beneath the specular reflection reducing element. The specular reflection reducing element can rest directly on the surface of the sample solution. The specular reflection reducing element can include a liquid and a solid.

In general, in one aspect, the invention provides methods and apparatus, including computer program products, implementing and using techniques for collecting optical data pertaining to one or more characteristics of one or more samples using scatterometry techniques. The apparatus includes a light source, a substrate, one or more illumination optical elements and one or more collection optical elements. The substrate has formed therein several sample wells. Each sample well is configured to hold a sample solution containing objects that are to be characterized based on their light scattering properties. At least some of the sample wells include a specular reflection reducing element for reducing specular reflections of light into one or more detectors. The illumination optical elements direct a light beam from the light source onto the objects in the sample wells. The collection optical elements collect light scattered by the objects in the sample wells and transmit the collected light to one or more detectors.

In general in one aspect, the invention provides a multi-well plate cover for use in collecting optical data pertaining to one or more characteristics of one or more samples using scatterometry techniques. The multi-well plate cover includes several specular reflection reducing elements. Each specular reflection reducing element fits into a sample well on a multi-well plate and contacts with the sample solution in the sample well so as to apply a uniform pressure to the sample solution and reduce a curvature of a meniscus of the sample solution, whereby unwanted reflections of light into one or more detectors are reduced when the sample wells are interrogated using a scatterometry system.

Advantageous implementations can include one or more of the following features. The specular reflection reducing element can be a solid, a plastic, a glass, a flexible solid, or a hard solid. The specular reflection reducing element can absorb light in a wavelength region corresponding to the wavelength region of the light source in a scatterometry system used to interrogate the sample wells in the multi-well plate. Each specular reflection reducing element can have an index of refraction close or equal to the index of refraction of the sample solution in its associated sample well. The specular reflection reducing elements can be sterilized prior to applying the specular reflection reducing elements to the sample solutions. The specular reflection reducing elements can be configured to be oriented at an angle with respect to the sample solution's surface when the multi-well plate cover is placed onto the sample wells so as to avoid trapping of air bubbles beneath the specular reflection reducing element The details of one or more embodiments of the invention are set forth in the accompanying drawings and the description below. Other features and advantages of the invention will be apparent from the description and drawings, and from the claims.

DETAILED DESCRIPTION

Reference will now be made in detail to specific embodiments of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, specific details are set forth in order to provide a thorough understanding of the present invention. The present invention may be practiced without some or all of these specific details. In addition, well-known features may not have been described in detail to avoid unnecessarily obscuring the invention.

The invention provides method and apparatus for reducing the undesired light reflections, for example, from the meniscus, thereby improving the abilities to view the cells in the sample solution. Some exemplary embodiments will be discussed below, but it ought to be clear to one of ordinary skill in the art that many variations can be accomplished which are within the spirit and scope of the invention as defined by the appended claims.

Figure 1:
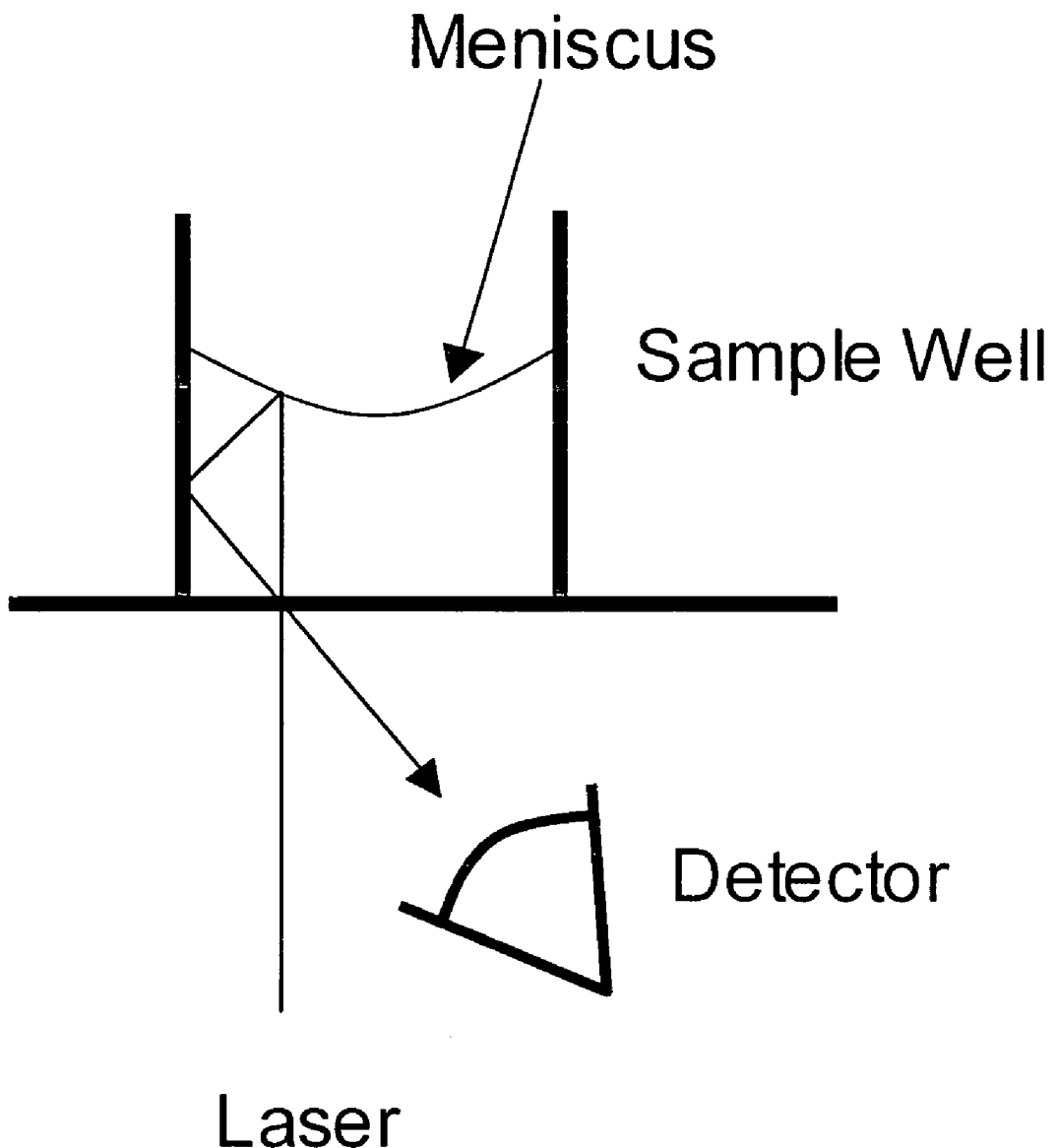
FIG. 1 is a schematic view of how reflections arise during scatterometry measurements in prior art applications.
Figure 2:
FIG. 2 shows the appearance of reflections in an image of a sample well containing a biological sample in prior art applications.
Figure 4:
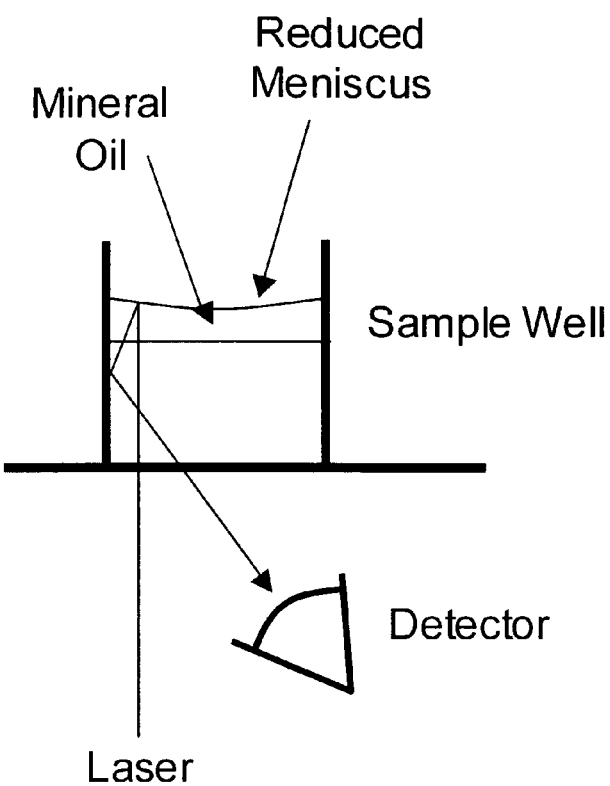
FIG. 4 is a schematic view of how reflections can be reduced in accordance with a first embodiment of the invention.

In a first embodiment, which is shown in FIG. 4, the curvature of the meniscus of the sample is reduced by applying a liquid on top of the sample prior to performing a scatterometry measurement. As can be seen in FIG. 4, the reduced curvature of the meniscus causes only the incident light close to the walls of the sample well to be reflected by the meniscus into the detector, whereas in FIG. 1, even light that is incident close to the center of the sample well gets reflected back into the detector, due to the larger curvature of the meniscus. The improvement in meniscus reflection can be seen in FIG. 5, which is an image of the same well that is shown in FIG. 2, but with a liquid coating applied.

Some examples of suitable liquids include mineral oils, glycerol, perfluorinated polyethers, and so on. Generally, it is advisable to select a liquid that has a refractive index that is as closely matched (for example within about 10%) with the refractive index of the sample solution as possible, since this will reduce the reflections at the sample solution/liquid interface. The liquid can be applied to the sample manually or automatically, through a number of conventional techniques, such as automated pipettors or liquid injectors. Typically, the thickness of the liquid layer above the sample is in the range of 100 micrometers to 10,000 micrometers. In some embodiments, the liquid can be dyed prior to applying the mineral oil to the sample. The color of the dye can be chosen such that it absorbs light in the wavelength range of the light source that is used in the scatterometry measurements, which further reduces the light that is reflected back to the detector from other surfaces.

Figure 3:
FIG. 3 shows the appearance of reflections in an image of a sample well containing a biological sample in prior art applications.
Figure 5:
FIG. 5 shows the reduction of reflections of the sample well in FIG. 2 as a result of applying the specular reflection reducing element in accordance with the first embodiment of the invention.
Figure 6:
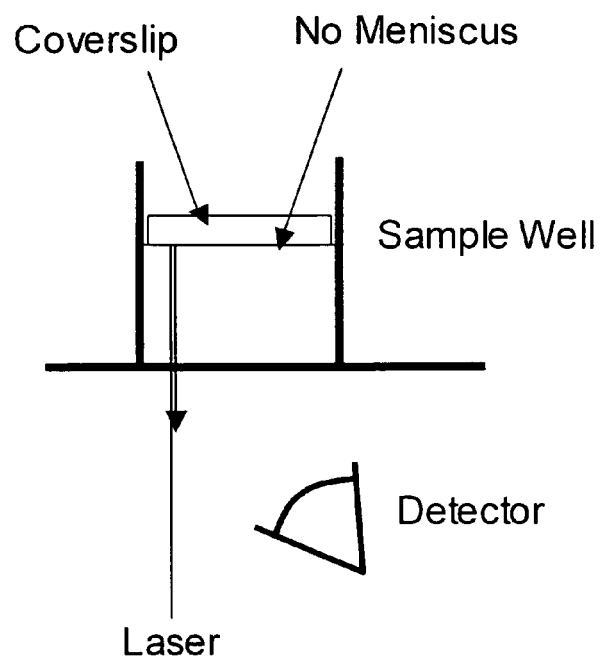
FIG. 6 is a schematic view of how reflections can be reduced in accordance with a second embodiment of the invention.
Figure 7:
FIG. 7 shows the reduction of reflections of the sample well in FIG. 3 as a result of applying the specular reflection reducing element in accordance with the second embodiment of the invention.

In a second embodiment, which is shown in FIG. 6, the meniscus of the sample is completely flattened, or almost completely flattened, by applying an optically flat coverslip on top of the sample prior to performing a scatterometry measurement. As can be seen in FIG. 5, no or little light is reflected by the liquid/coverslip interface into the detector. The improvement in meniscus reflection in this second embodiment can be seen in FIG. 7, which is an image of the same well that is shown in FIG. 3, but with a coverslip applied. It should also be noted that when comparing FIG. 3 and FIG. 7, it can be seen that the cells (which are visible as bright spots in the images) remain in the same positions both prior to the application of the coverslip (i.e., FIG. 3) and after the application of the coverslip (i.e., FIG. 7). That is, the cells have not been disturbed by the application of the coverslip.

Some examples of suitable coverslip materials include Plexiglas, polycarbonate, glass, and acrylic. Similar to the first embodiment described above, it is advisable to select a coverslip material that has a refractive index that is as closely matched with the refractive index of the sample solution as possible, since this will reduce the reflections at the sample solution/coverslip interface. In some embodiments, the coverslip can be made of a colored material that absorbs light in the wavelength range of the light source that is used in the scatterometry measurements, which further reduces the light that is reflected back to the detector. Depending on the absorption properties of the colored coverslip, the requirements of having an optically flat coverslip may be reduced. That is, if a sufficient amount of light is absorbed by the coverslip, then it may be less important that the coverslip is optically flat.

In some embodiments, the coverslips are sterilized prior to placing them on top of the sample. For example, when cells are grown in colonies and are used to produce antibodies, it is important not to disturb the sample and to keep the cells sterile and alive. In such situations, it is necessary to use a sterilized coverslip in order to achieve the reduced unwanted reflections.

It should be noted that the way in which the coverslip is applied to the solution often determines the degree to which the unwanted reflections can be reduced. For example, it is important that air bubbles do not get caught in the sample solution under the coverslip when the coverslip is being applied. One method of avoiding this is to apply the coverslip at an angle with respect to the surface of the sample solution. This can be achieved in numerous ways that are familiar to those of ordinary skill in the art. For example, the coverslips can be applied by various manual techniques. However, typically this involves applying coverslips to one well at a time, which may be both time consuming and error prone, especially when a large number of wells is present, such as on a conventional 96-well plate. In such a situation, it may be preferable to have a single multi-well cover, on which coverslips for the individual wells are mounted, for example, with each coverslip being mounted on a "rocker" that allows the coverslips to have a first position while the cover is applied to the wells, and a second position after the cover is placed onto the wells. In this way, all the wells can have their respective coverslips applied at the same time and at an angle, and after the application the coverslips "rock" into place and rest on the sample surfaces of the respective wells, as described above. Alternatively various types of suction cups using liquid dispensing tools can be used to place the coverslips into the wells. It should be noted that irrespective of the method used, it is important to pay attention in applying the coverslip such that no air bubbles are trapped below the coverslip, and so that no scratches or marks are made on the coverslip during the application process, which may introduce additional unwanted reflections.

The choice between using a coverslip or using a liquid to reduce the unwanted reflections depends not only on the severity of the reflections, but also on a number of factors related to the type of experiment that is performed and the type of sample that is used. For example, if the sample will be discarded after the scatterometry measurements have been performed, then a mineral oil might be a good choice. On the other hand if the sample needs to be investigated repeatedly over the course of several days, potentially with different agents being added to the sample in between the investigations, then a coverslip might be a better choice.

Figure 8:
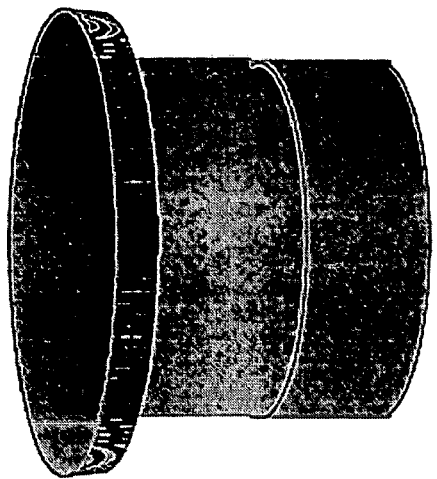
FIG. 8 is a schematic view of how reflections can be reduced in accordance with a third embodiment of the invention
Figure 8:
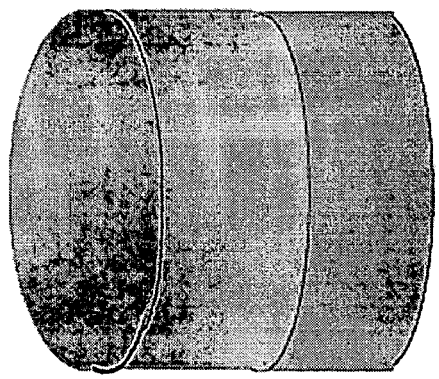
Figure 8:
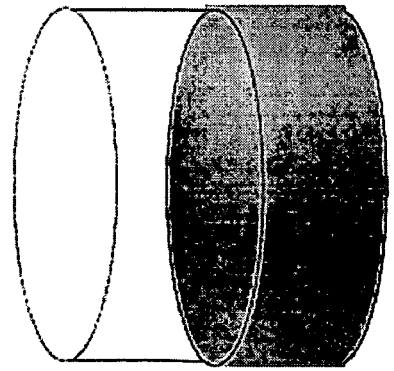

In some embodiments, a combination of a coverslip and a liquid may be used. For example, it may be difficult or time consuming to apply individual coverslips to all wells in a 96-well plate. In these cases, the embodiment shown in FIG. 8 may be appropriate. As can be seen in FIG. 8, each sample well is first overfilled with a suitable liquid, and then a coverslip is placed on top of the overfilled sample well. One benefit of this approach is that a single coverslip or lid may be used to cover all the sample wells on a sample plate. It should however be noted that it is also possible to use individual coverslips for the wells. The solution can be selected such that its refractive index is the same or close to the refractive index of the medium in which. the cell colonies are grown. In one embodiment, the same type of medium is used for growing cells and for overfilling the respective sample wells. In some embodiments, the overfill liquid and/or the coverslip may be colored in order to absorb light from unwanted reflections.

The embodiments described above are merely examples of a general technique of reducing or eliminating the curvature of the meniscus and otherwise eliminating unwanted reflections by placing something on top of the sample liquid. Other materials can also be used, such as gels, oils, solid, plastics, glasses, flexible solids, hard solids, and waxy-like materials that change properties based on their temperature can also be used As was discussed above, various combinations of liquids and solids may also be used. Applying any of these materials causes the meniscus surface of the sample liquid to flatten. Many of these materials can also be selected such that their indexes of refraction are closely matched with the index of refraction for the sample solution. Many of the materials also absorb light, either inherently, or can be pre-processed such that they will absorb light in a predetermined wavelength range when they are applied to the sample.

The techniques described above can be used in a variety of assays. For example, in conventional drug discovery programs, researchers wish to determine the potency of particular drug candidates. Potency is typically expressed in terms of cell killing ability, inhibition ability, etc. Modes of expressing such potency include EC50 values, IC 50 values, and the like. Various assays are employed to gather such information.

A classical approach known as the "clonogenic assay" evaluates cell growth after treatment. It does this by exposing cultured cells to a compound of interest for a defined period of time. Frequently, different cell cultures are exposed to the compound at multiple different concentrations and for different periods of time. After the requisite exposure times, the cell cultures are washed to remove the compound and a fixed number of cells at each condition are replated at low density. Then after some additional time has elapsed, the surviving cells will grow into small colonies, which are counted and compared, to the number of cells that were originally plated. Cells that are strongly impacted by the compound may be replated as living cells but will not thrive. Using the colony counts, one can assess the health and growth potential of the survivors. The end result may be a graphical representation of survival versus drug concentration called a cell survival curve. IC50 values may also be obtained from the concentration dependence of the compound.

The traditional assay is done manually such that after washing, surviving cells are removed and re-plated into agar dishes. Typically, the cells are trypsinized (treated with the proteolytic enzyme trypsin) to remove them and the living cells are selected for replating. In one example, about 100 live cells are harvested and replated. The harvested cells are then allowed to grow for a period of time, typically about one week or 10 days. They are then stained and imaged and the colonies that they form are manually counted. As indicated, the compound's potency is assessed from the relative counts.

Conventionally clonogenic assays are used to evaluate various types of stimuli, including radiation that might be employed to kill tumor cells, but as the skilled person realizes, virtually any potential cellular stimulus that is discoverable using scatterometry techniques may be studied using this invention. This includes stimuli having positive as well as negative effects on cell growth. In other words, a stimulus under investigation may promote as opposed to inhibit cell growth; e.g., the stimulus may be a factor that stimulates growth of osteocytes or neurons.

An apparatus suitable for performing scatterometry analysis of the sample wells discussed above, has been described in U.S. patent application Ser. No. 10/927,748 entitled "TIME DEPENDENT FLUORESCENCE MEASUREMENTS" filed on Aug. 26, 2004, and in U.S. patent application Ser. No. 10/928,484 entitled "MEASURING TIME DEPENDENT FLUORESCENCE" filed on Aug. 26, 2004, the entire disclosures of both of which are incorporated herein by reference for all purposes. The description of the apparatus and methods in these two patent applications is focused on fluorescence applications, but as the skilled person realizes, the apparatus and methods are equally applicable to performing scatterometry measurements, with some minor modifications that will be described in detail below. Generally, the apparatus that uses a scanning light source, which can be focused onto an array of samples or objects, with the ability to discriminate against background noise or signal, and makes use of image contrast mechanisms. The apparatus of the invention can be operated in several distinct modes or combinations thereof, depending on what type of scatterometry data needs to be collected. A high-level description of some exemplary modes will first be provided, followed by a more detailed discussion highlighting some specific features of the apparatus that are important for scatterometry applications.

In a first mode, the output signal from the apparatus contains information such as the number of discrete positions in a cell or other object from which the scattered light originates, and the relative location of the scattering objects. As a result of the geometry of the illumination optics, a relatively large illumination region is created that is confined to a region within the sample volume, thereby eliminating the need to have an apparatus which must adjust the focus of the illumination continuously and in real time over a plurality or an array of samples. The geometry of the collection optics limits the detection region to a focal volume where the sample is contained and from which the data is collected. In one embodiment, multiple collection arrangements are used with the attendant benefits, which will be described below for a setup with two collection lenses.

In a second mode, a plane-polarized laser beam can be propagated through the optical system onto the sample, allowing interrogation of the biological material with polarized light. In this mode the scattered light can be separated into its two orthogonal components and analyzed either sequentially in time with a switchable modulator, such as an electrooptic modulator, to allow for detection of the parallel and perpendicular components, or simultaneously with multiple collection optics with specified perpendicular and parallel polarizing filters. The polarization is important, because if the object that scatters the light has a particular orientation, then the scattering efficiency of the object will be a function of the incident light polarization. In some embodiments, the polarization can be aligned such that scattered light from surface scratches of the sample well or the coverslip (which are highly oriented) is minimized, while scattered light from cell colonies (which have no or little orientation) is maintained. Another example where polarization comes into effect is that "point scattering," that is, a single scattering event such as a surface scratch, gives rise to scattered light with high polarization or anisotropy. In contrast, "volume scattering," that is, where multiple scatter events occur before the light exits the "scattering volume" gives rise to scattered light that is more depolarized. Specular reflections are always highly polarized. Thus, when studying scattered light from three-dimensional cell colonies, the scattered light will be depolarized, but any specular light or scatter from scratches will be highly polarized and can be filtered out using a polarization filter.

In a third mode, several laser beams can be propagated through the optical system onto the sample allowing interrogation of the biological material with different wavelengths of light or with the same wavelength at different times. In this mode the lasers can be pulsed simultaneously or with a fixed or variable delay between pulses. As is well known in the art, the wavelength of the illumination light is important since the scattering efficiency is proportional to the frequency of the light to the fourth power. For this reason, in some embodiments, blue lasers are used as light sources, along with coverslip materials or liquid dyes that have high extinction coefficients for blue light.

In a fourth mode, several detectors can be used in conjunction with one collection optics arrangement, which creates multiple confinement regions for analysis, the advantages of which will be described in further detail below.

In a fifth mode, several collection optics arrangements can be used to provide improved confinement over a single collection optic with the unique geometry, or can be used to collect scattering from the confined region with several characteristics which are uniquely specified to each collecting optics, the advantages which will be described below.

Figure 9:
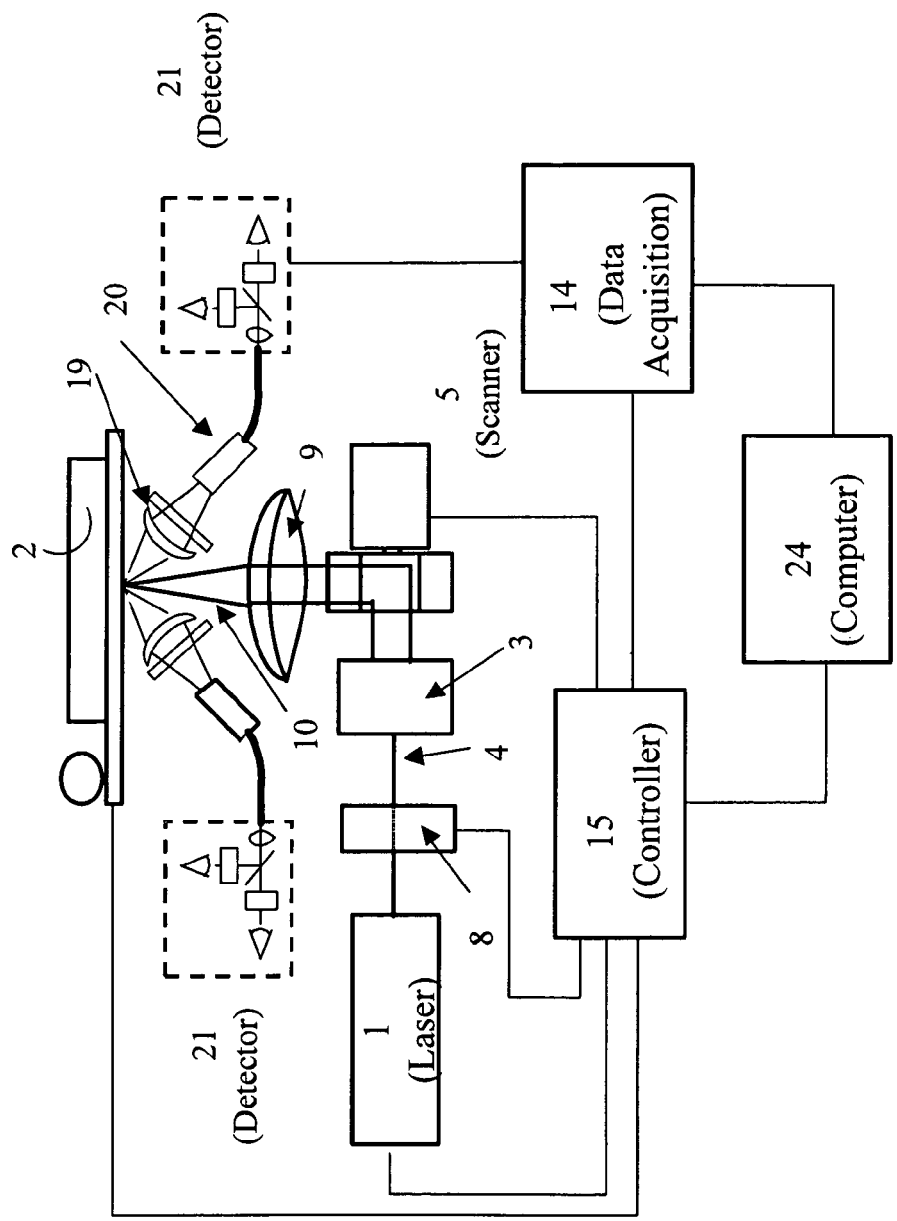
FIG. 9 is a schematic view of an apparatus for collecting optical scatterometry data from a sample well in accordance with the invention.

The apparatus will now be described in further detail, by way of example, with reference to FIGS. 8-10. As shown in FIG. 9, in one embodiment, a light source (1) emits light (4) to be projected onto a sample (2) that is to be investigated and which rests on a microarray plate. Typically, the light source (1) is a laser, such as an Ar or Ar/Kr mixed gas laser with wavelengths of 488, 514, 568 and 647 nm, respectively. In one embodiment, a continuous wave (CW) laser, such as the Picarro Cyan laser from Picarro Inc. of Sunnyvale, Calif., is used as a light source. Depending on the laser (1) and specific optics used in the apparatus, the wavelength of the light source can be either within the visible range (i.e., 400-700 nm), or outside the visible range. For example, outside the visible range, near infrared light exhibits good tissue penetration, such that tissue samples can be investigated using scatteromery techniques. Ultraviolet light, on the other hand, exhibits more efficient scattering. However, it should be noted that using wavelengths outside the visible range places additional requirements on the sample wells or multiwell plates that are used in terms of what wavelength regions they can transmit.

It should be noted that the illumination light does not have to be a laser, nor does it have to be a narrow band light source. However, lasers are advantageous to use, since they have a high photon fluence that makes it possible to measure scattering of light off very small objects. Also the polarization of a laser can be exploited, as mentioned above, although "white light" or LED light sources can also be polarized. In the particular embodiment described herein, there is a need for a focused beam of light that can be scanned across a surface, so a laser is a preferable light source. As was noted above, it is preferable to use colored coverslips or liquids that absorb light. This is another good reason for using a laser as a light source, since the wavelengths of the laser typically are very well-defined and can easily be matched with the absorption wavelengths of the coverslip or liquid. However, depending on the sensitivity of the detectors, white light illumination is also possible, as is typically employed in applications where surface scratches and defects are examined.

After leaving the laser (1), the illumination light (4) passes through one or more illumination optical elements to the sample (2). The illumination optical elements include an electro-optic modulator (8), a set of beam-shaping lenses (3), a scanning device (5), and a multi-element lens (9). The electro-optic modulator (8) can be used to polarization modulate the illumination light (4), if required by the investigation that is to be carried out on the sample (2). The set of beam-shaping lenses (3) expands the laser beam in order to match the input aperture of the scanning lens and provide the desired illumination region size at the sample (2). The scanning device (5) moves the expanded laser beam back and forth in a line-scan over the sample (2) after the beam has been focused by the multi-element lens (9). The scanning device (5), which will be described in further detail below, can be an electromechanical device coupled to an optic element, such as a mirror driven by a galvanometer. In one embodiment, which will also be described in further detail below, the scanning device (5) uses a polygon with multiple reflective surfaces to scan the laser beam across the sample (2). The multi-element lens (9) is designed to focus the laser light at the operating wavelength of the laser (1). The multi-element lens (9) can, for example, be a microscope objective designed for the operating wavelength or a specially designed scanning lens, such as a telecentric lens, that has appropriate parameters to achieve a flat focal plane, for example, with a long working distance and low first and second order aberrations, thus producing the same spot size and shape over a wide range of positions (such as a scan line). The telecentric lens is particularly useful for covering a large field of view.

After passing the multi-element lens (9), the beam (10) is focused onto a region of the sample (2) to be imaged. The focal region is located above, for example, a base of a microarray plate. The sample (2) can be objects to be interrogated by scatterometry, such as cells contained in a sample well, as described above.

The scattered light emitted by the sample (2) is collected by one or more collection optical elements (19). As will be discussed below, there are several ways to configure the collection optical elements (19) that allow scanning of a large array, such as microarray plate. In one embodiment, the collection optical elements (19) is a rod lens, designed to capture the entire range of sweep of the beam (10) over one dimension of the base (11) of the sample array. The collection optical elements (19) can also include other types of lenses, or an aggregate of lenses, as would be determined by the specific information required from the emission. In some embodiments, multiple setups of collection optical elements (19) can be used to improve collection efficiency.

The light collected by the collection optical elements (19) is transmitted to a detector (21) located at a convenient distance from the collection optical elements (19). The transmission of the scattered light can be accomplished by, for example, an optical fiber or a bundle of optical fibers (20). In one embodiment, the detector (21) is a detector with high gain, such as a photomultiplier tube, which produces an electrical output signal. The electrical output signal is further processed by a data acquisition system (14), which performs operations such as optimization of the gain and the signal to noise ratio (S/N), by making use of signal enhancing, averaging, or integrating detection systems.

The multi-element lens (9) that receives the laser light (4) is designed to focus the laser light at the operating wavelength of the laser (1). The multi-element lens (9) focuses the laser light (4) close to the diffraction limit of the multi-element lens (9), which is typically in the range of 5-20 microns, but can be as small as large as 1-200 microns. The sample or sample array (2) is arranged to accept the focused, beam at, or just above, the base (11) of the sample (2). The length of the scan line across the sample array (2) can be varied and is typically in the range 5 mm to 100 mm.

Figure 10:
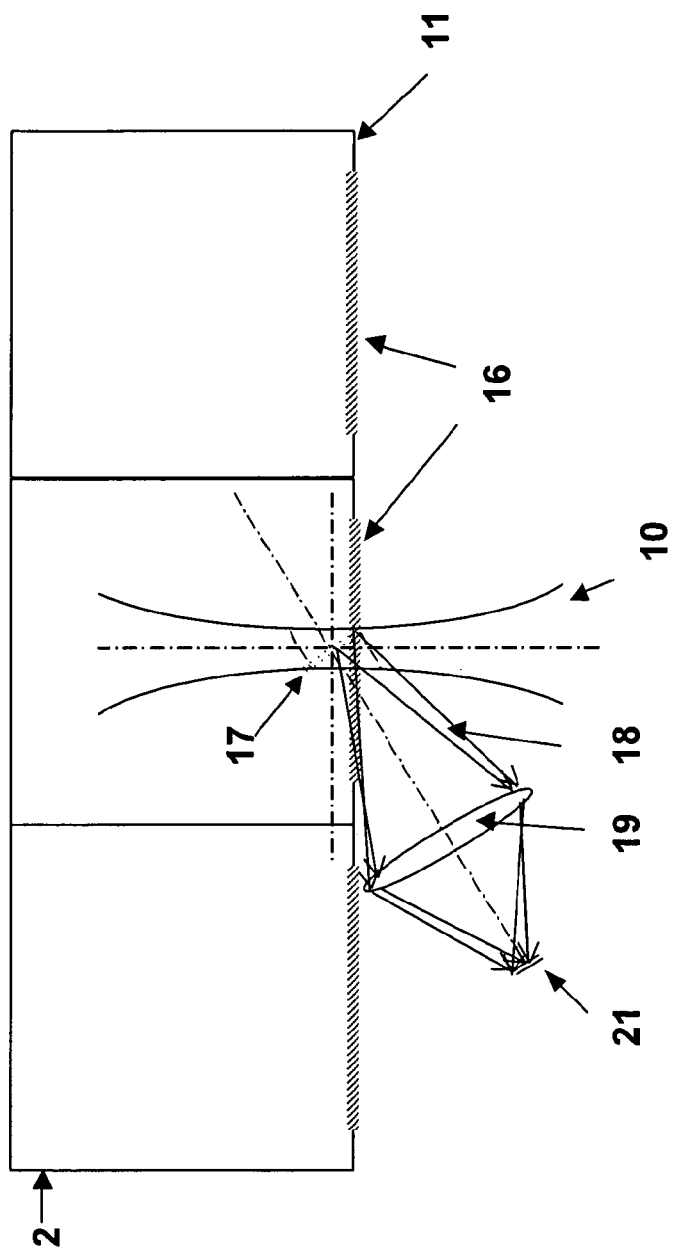
FIG. 10 is a schematic diagram showing a confined field of view for a single detector configuration of the apparatus of FIG. 9.

FIG. 10 shows an enlarged view of the sample (2), how incoming light (10) illuminates the sample (2), and a source region (17) from which the scattered light is collected in a single detector embodiment of the apparatus of FIG. 9. The sample (2) is located on a base (11) with a series of optical elements (16) that allow the laser light (10) to be transmitted through to the sample contained in the array. The array can, for example, be a microarray plate containing wells with solutions or samples adhered to the bottom of the wells. The focal plane location is near the inner side of optical elements (16) and defines the region of highest light flux, thereby defining a region of highest emitted light source. The region's volume size depends on the multi-element lens (9) configuration and the depth of the interrogated sample (2) located above the base (11). The defined volume of a source region (17), which actually gives rise to the scattered signal, additionally depends on the configuration of the collection optical elements (19), as will now be discussed.

As can be seen in FIG. 10, the geometry of the collection optical elements (19) is such that the collection region is confined to the region of the field of view for the detector (21). The scattered signal intensity is confined to a source region (17) formed by the intersection of the light source's focal region and the image of the detector (21) inside this region, as shown in FIG. 9. The source region is located within a limited vertical depth of the sample, that is, at a limited distance range above the base (11) upon which the sample (2) rests. A number of advantages result from arranging the collection optical elements (19) such that a collection path (18) forms an angle with the incident light (10). For example, the need for optically flat sample wells that do not deviate in the location of surface apertures (16) of the wells (2) is eliminated. The collection region is fixed or confined by the collection optical elements (19) configuration so as to not be out of the focal plane of the system. Another advantage is that high signal discrimination from background scattering in the sample well is accomplished.

The scattered light from the source region (17) is transmitted to the collection optical elements (19) along the collection path (18). The collection path (18) can extend through the optical element (16) in the base (11) of the sample well, as shown in FIG. 10. In an alternative embodiment, the collection path can extend through the well in the sample array to a location on the opposite side of the sample array, as shown in FIG. 9, for example. In both embodiments, the collection optical elements (19) are configured to collect and focus the scattered light from the source region, as was described above.

Figure 11:
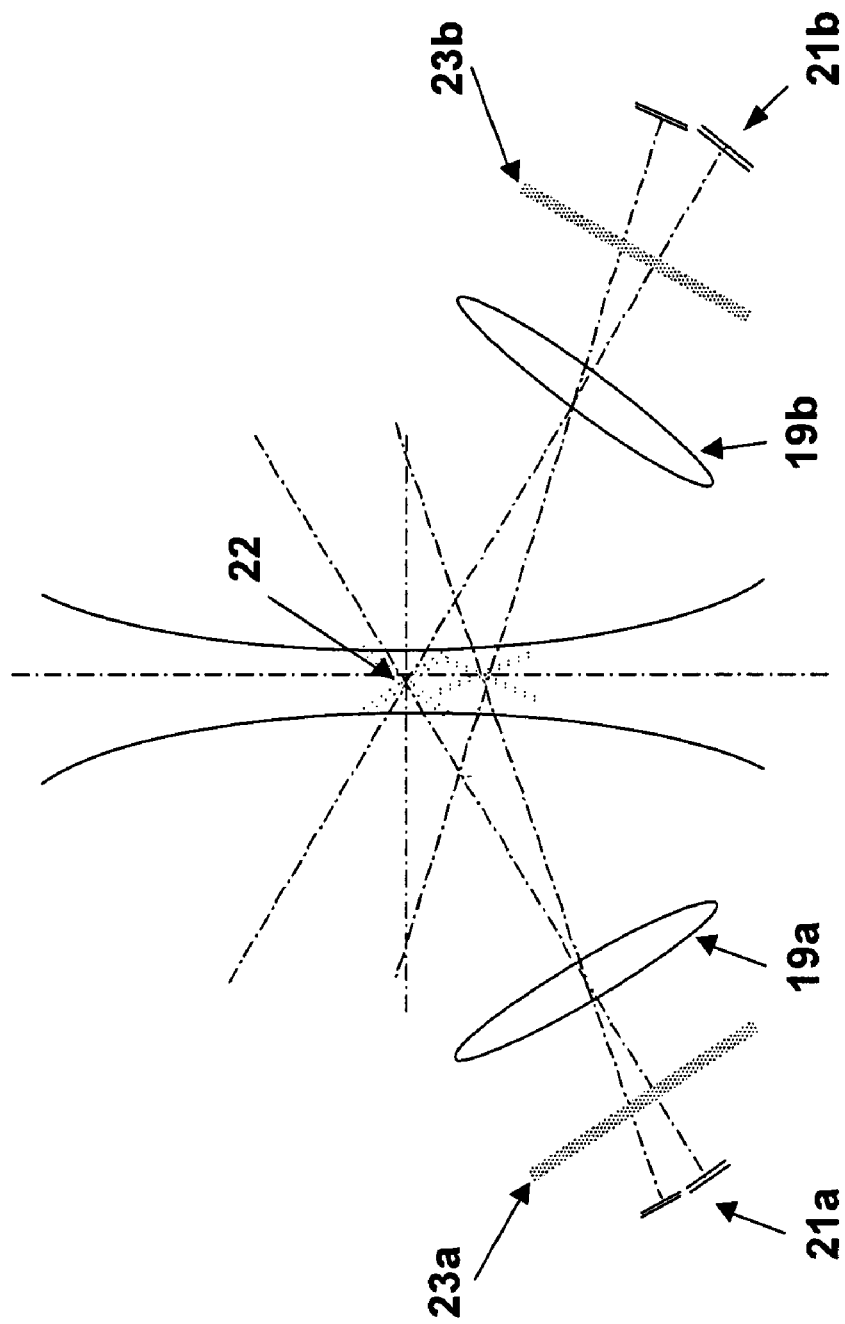
FIG. 11 is a schematic diagram showing a confined field of view in a stereo configuration of the apparatus of FIG. 9 with multiple detectors shows Like reference symbols in the various drawings indicate like elements.

Various details and alternative ways of configuring the collection optical elements (19) have been disclosed in the above referenced patent applications and will therefore not be disclose in any detail herein. However. one embodiment, which is shown in FIG. 11, has been shown to be particularly useful. As can be seen in FIG. 11, two or more collection optics arrangements (19a, 19b) are provided. With a stereo configuration of the collection lenses (19a, 19b) as shown in FIG. 11, the focal field for the two lenses can have improved confinement over the single field generated by one lens and the focusing source shown and discussed above with respect to FIG. 10. The improvement is schematically represented in FIG. 11 by the intersection (22) of the focal planes for the respective collection optics arrangements (19a, 19b), corresponding to the main object planes of the lenses (19a, 19b).

The setup of FIG. 11 with two sets of collection optics (19a, 19b) can also be used for simultaneous collection of orthogonal components of emission from a polarized light source. A first polarizing filter (23a) can be used to pass only light of a first polarization to a first detector (21a), and a second polarizing filter (23b) can be used to pass only light of a second, orthogonal, polarization to a second detector (21b). The correlation of the signals collected in this configuration, detection in the detection system, and subsequent manipulation of the stored signal give rise to information not available to a single detector, with attendant improvement in signal.

Generally, it should be noted that the placement of the detectors is very important for picking up scattered light. An object and illumination system will have a Bidirectional Scatter Distribution Function (BSDF). which describes the intensity of scattered light into a given angle. Some objects scatter more into small angles, while other objects scatter more into large angles. In the above-described embodiment of the analysis system, a very large range of angles can be recorded due to the high numerical aperture of the detector optics, which results in a very efficient scatterometry system. A potential downside may be the lack of ability to discriminate between large and small angles, which may limit the range of applications in which the analysis system can be used. However, as the skilled person in the art realizes, this potential drawback relates to the analysis system as such, and not to the inventive methods and apparatus for reducing the meniscus scattering, as described herein.

A number of embodiments of the invention have been described. Nevertheless, it will be understood that various modifications may be made without departing from the spirit and scope of the invention. For example, while a continuous scanning mode of interrogating the individual samples has been described, other techniques such as a parallel illumination or stepping may be employed. The above description has been focused on biological applications and scattering off single cells, but it should also be noted that the same principles apply to larger objects, such as cell colonies, or to smaller objects, such as various sub-cellular features. The apparatus and methods described above can also be used to detect non-organic substances in air or liquids. Accordingly, other embodiments are within the scope of the following claims.

The invention claimed is:

1. A method for collecting optical data pertaining to one or more characteristics of one or more liquid sample solutions using scatterometry techniques, comprising:
    providing a substrate having formed therein one or more sample wells, each sample well being configured to hold a liquid sample solution containing objects that are to be characterized based on their light scattering properties;
    dispensing the one or more liquid sample solutions into the plurality of sample wells;
    applying a specular reflection reducing element to at least some of the liquid sample solutions at an angle with respect to the liquid sample solution's surface so as to avoid trapping of air bubbles beneath the specular reflection reducing element in the plurality of sample wells to decrease reflections of light from the liquid sample solutions into one or more detectors;
    directing a light beam from a light source onto the objects in the sample wells;
    collecting light scattered by the objects in the sample wells and transmitting the collected light to one or more detectors; and
    analyzing the signal from the detectors to detect the one or more characteristics of the one or more liquid sample solutions.

2. The method of claim 1, wherein the specular reflection reducing element is one of: a gel, an oil, a solid, a plastic, a glass, a flexible solid, a hard solid, and a waxy-like material.

3. The method of claim 1, wherein the specular reflection reducing element is configured to reduce a curvature of a meniscus of the liquid sample solution.

4. The method of claim 1, wherein the specular reflection reducing element is configured to absorb light in a wavelength region corresponding to the wavelength region of the light source in order to further reduce reflections.

5. The method of claim 1, wherein the specular reflection reducing element has an index of refraction close to or equal to the index of refraction of the liquid sample solution.

6. The method of claim 1, further comprising sterilizing the specular reflection reducing elements prior to applying the specular reflection reducing elements to the at least some liquid sample solutions.

7. The method of claim 1, wherein the specular reflection reducing element rests directly on the surface of the liquid sample solution.

8. The method of claim 1, wherein the specular reflection reducing element comprises a liquid and a solid.

9. An apparatus for collecting optical data pertaining to one or more characteristics of one or more liquid sample solutions using scatterometry techniques, the apparatus comprising:
    a light source;
    a substrate having formed therein a plurality of sample wells, each sample well being configured to hold a liquid sample solution containing objects that are to be characterized based on their light scattering properties, wherein at least some of the sample wells of the plurality of sample wells include a specular reflection reducing element applied at an angle with respect to the sample solution's surface so as to avoid trapping of air bubbles beneath the specular reflection reducing element and operable to reduce specular reflections of light from the liquid sample solutions into one or more detectors;
    one or more illumination optical elements for directing a light beam from the light source onto the objects in the sample wells;
    one or more collection optical elements for collecting light scattered by the objects in the sample wells and transmitting the collected light to one or more detectors.

10. The apparatus of claim 9, wherein the specular reflection reducing element is one of: a gel, an oil, a solid, a plastic, a glass, a flexible solid, a hard solid, and a waxy-like material.

11. The apparatus of claim 9, wherein the specular reflection reducing element is configured to reduce a curvature of a meniscus of the liquid sample solution.

12. The apparatus of claim 9, wherein the specular reflection reducing element is configured to absorb light in a wavelength region corresponding to the wavelength region of the light source in order to further reduce reflections.

13. The apparatus of claim 9, wherein the specular reflection reducing element has an index of refraction close to or equal to the index of refraction of the liquid sample solution.

14. The apparatus of claim 9, wherein the specular reflection reducing elements are sterilized prior to placing them in the sample wells.

15. The apparatus of claim 9, wherein the specular reflection reducing element rests directly on the surface of the liquid sample solution.

16. The apparatus of claim 9, wherein the specular reflection reducing element comprises a liquid and a solid.

* * * * *

UNITED STATES PATENT AND TRADEMARK OFFICE
CERTIFICATE OF CORRECTION

PATENT NO.       : 7,643,146 B2                                          Page 1 of 1
APPLICATION NO.  : 11/336388
DATED            : January 5, 2010
INVENTOR(S)      : Cromwell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 158 days.

Signed and Sealed this

Sixteenth Day of November, 2010

David J. Kappos
*Director of the United States Patent and Trademark Office*